United States Patent [19]
Burkovich et al.

[11] Patent Number: 5,441,891
[45] Date of Patent: Aug. 15, 1995

[54] TRANSFER MECHANISM WITHIN AN INCUBATOR

[76] Inventors: Robert A. Burkovich; James D. Riall, both of Eastman Kodak Company, Rochester, N.Y. 14650

[21] Appl. No.: 249,501

[22] Filed: May 26, 1994

[51] Int. Cl.⁶ ............................ G01N 35/00; G01N 37/00
[52] U.S. Cl. ............................ 436/48; 422/63; 422/64; 422/67; 436/43; 436/47; 435/809
[58] Field of Search ............... 422/63, 64, 100, 67; 436/43, 48, 180, 47; 435/809

[56] References Cited

U.S. PATENT DOCUMENTS

| | | | |
|---|---|---|---|
| 4,406,547 | 9/1983 | Aihara | 356/414 |
| 4,476,733 | 10/1984 | Chlosta et al. | 73/863.91 |
| 4,595,562 | 6/1986 | Liston et al. | 422/65 |
| 4,699,766 | 10/1987 | Yamashita | 422/64 |
| 4,713,974 | 12/1987 | Stone | 73/864.23 |
| 4,755,055 | 7/1988 | Johnson et al. | 356/440 |
| 5,244,633 | 9/1993 | Jakubowicz et al. | 422/64 |

Primary Examiner—James C. Housel
Assistant Examiner—Long V. Le
Attorney, Agent, or Firm—Dana M. Schmidt

[57] ABSTRACT

An incubator and method of transfer in such incubator in an analyzer, wherein a simple transfer mechanism is provided for moving a cuvette from one incubator ring to another adjacent one. The mechanism comprises a shuttle disposed above said rotors, said shuttle having an aperture sufficiently large as to receive, but not retain by friction, one of said vessels, a mechanism for moving the shuttle and its aperture to traverse from one ring to the other, and a pusher member and mechanism for moving the pusher member to raise a cuvette from one ring into the shuttle. When the shuttle aperture aligns with the aperture of the other ring, a cuvette in the shuttle simply falls under the influence of gravity into the other ring.

16 Claims, 5 Drawing Sheets

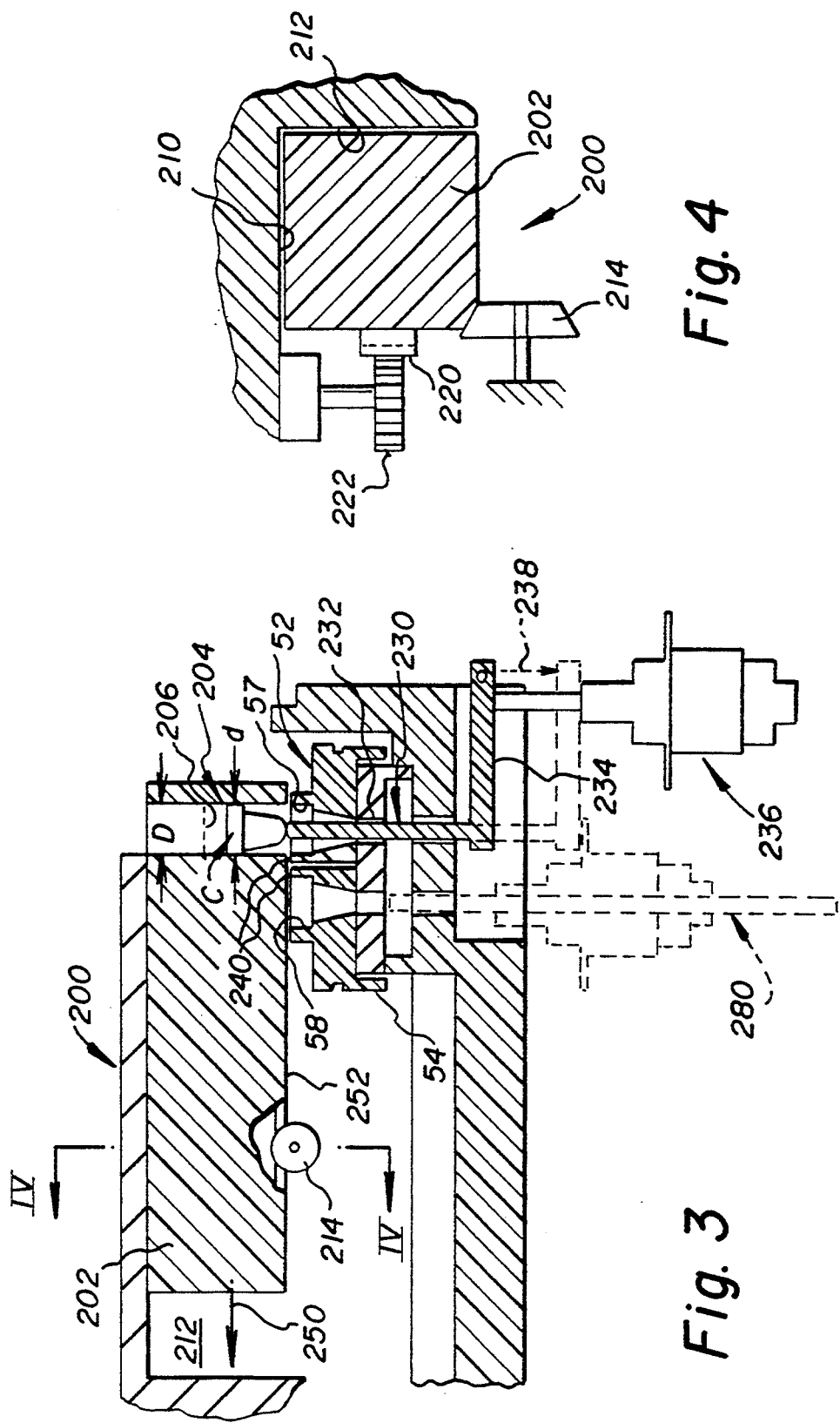

TRANSFER MECHANISM WITHIN AN INCUBATOR

FIELD OF THE INVENTION

The invention is directed to an incubator of an analyzer that uses reaction vessels, and more particularly, to a transfer mechanism for transferring the vessel within the incubator.

BACKGROUND OF THE INVENTION

It is common practice in incubators of reaction vessels containing sample and reagent, to process them by carrying them in two independently-driven, concentrically mounted rotors, using a transfer mechanism to move a vessel from one rotor to the other as needed, to complete the processing. Such devices are shown in, e.g., U.S. Pat. Nos. 4,699,766 and 5,244,633. In the former, the transfer occurs by an elevator that raises the vessel above the first rotor, moves it linearly to a position above the second rotor, and drops it into the second rotor. In the '633 patent, a push rod merely pushes the vessel across from one rotor to the other via slots located in the rotor for this purpose.

In either case, the transfer mechanism is quite elaborate. For example, the description in the '766 patent (column 4, lines 47–49) is of the use of an elevator that must grip the vessel, raise and move it linearly, lower it and then ungrip it (the details of which, however, are not shown). Such involved and complex mechanisms do not lend themselves either to a) inexpensive manufacture or b) reduced maintenance during operation.

Thus, there has been a need prior to this invention to provide a transfer mechanism between rotors of an incubator using, for example, an elevator that is simplified in construction, leading to reduced costs of manufacture and maintenance.

SUMMARY OF THE INVENTION

We have devised a transfer mechanism that meets the above-described need. It does this by relying on gravity to "lower" the vessel after linear transfer, thus doing away with the need for a gripping and ungripping mechanism.

More specifically, in accordance with one aspect of the invention there is provided an incubator comprising a first and a second rotor disposed adjacent each other, each comprising stations constructed to receive and incubate a vessel of liquid, means for independently rotating each of the rotors, and transfer means for transferring a vessel of liquid from one of the rotors to the other of the rotors. This transfer means comprises a shuttle disposed above the rotors, the shuttle having an aperture sufficiently large as to receive, but not retain by friction, one of the vessels; first means for moving the shuttle so as to cause it and the aperture to traverse from one of the rotors to the other; a pusher member; second means for moving the pusher member into the one rotor into contact with a vessel in the one rotor, and for raising the contacted vessel out of its station in the one rotor into the shuttle; the pusher member and the one rotor station being sized so as to hold a raised vessel within the shuttle aperture until the shuttle has started to move away from the one rotor; and a guide surface under the shuttle constructed to retain the raised vessel in the aperture until a station in the other rotor is reached, so that alignment of the shuttle aperture with an unoccupied station of the other rotor is sufficient to cause the raised vessel to fall out of the aperture into the unoccupied station.

In accordance with another aspect of the invention, there is provided a method for transferring a reaction vessel containing incubating liquid, from one rotor to another, the vessel being held in each of the rotors at a station, the method comprising the steps of a) raising a reaction vessel from its station in the one rotor to a position above the one rotor within an aperture of a shuttle, the aperture being sufficiently large as to receive, but not retain by friction, one of the vessels, b) moving the shuttle and the reaction vessel within the aperture from the one rotor to the other rotor, the pusher member and the one rotor station being sized so as to hold a raised vessel within the shuttle aperture until the shuttle has started to move away from the one rotor, c) and aligning the shuttle aperture with an unoccupied station of the other rotor, so that the vessel within the shuttle aperture falls into the unoccupied station.

Accordingly, it is an advantageous feature of the invention that a simplified transfer mechanism is provided for transferring a vessel from one incubator rotor to another, by relying in part on gravity.

Other advantageous features will become apparent upon reference to the detailed description that follows, when read in light of the attached drawings.

BRIEF DESCRIPTION OF THE DRAWINGS

FIG. 3 is a fragmentary elevational view in section of the transfer mechanism of the incubator;

FIG. 4 is a sectional view taken generally along the line IV—IV of FIG. 3;

DESCRIPTION OF THE PREFERRED EMBODIMENTS

The following description concerns the preferred embodiments in which the incubator is utilized in an analyzer of a preferred construction, with preferred stations that interact with the incubator, and wherein a reaction vessel is raised into a shuttle, and the shuttle is moved, all by preferred mechanisms. In addition, the invention is useful regardless of the construction of the rest of the analyzer or its interacting stations, and regardless of the construction of the shuttle and the mechanism for moving the shuttle, provided that the shuttle aperture does not retain the vessel vertically by friction, but instead will release the vessel to fall by gravity if there is nothing under the shuttle to prevent it from falling.

As used herein, "fall" or "falling" refers to the action of the vessel under gravity, whether or not the vessel actually undergoes free-fall before it is received by the structure below it.

Figure 1:
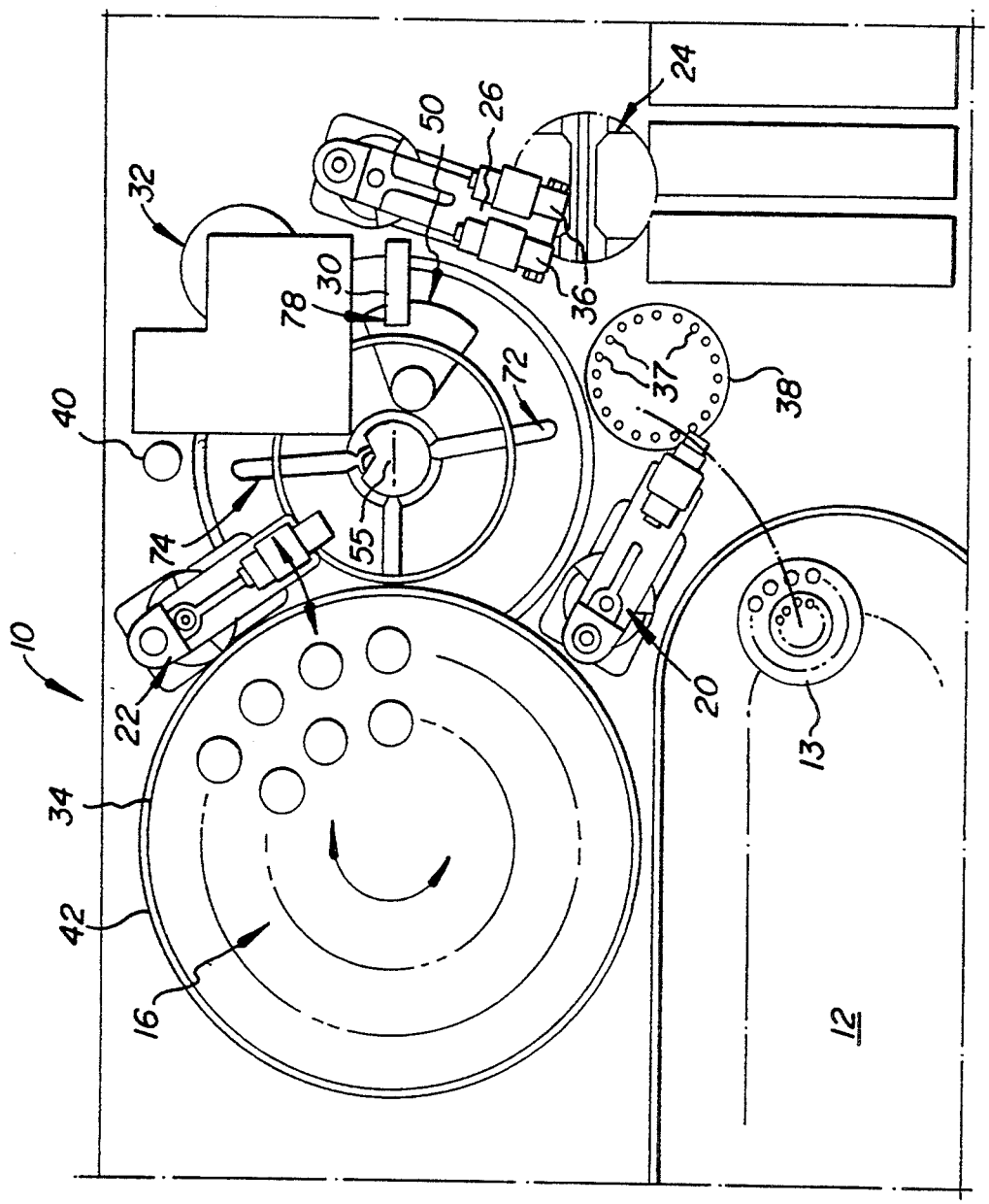
FIG. 1 is a fragmentary plan view of an analyzer in which the incubator of the invention is useful.
Figure 2:
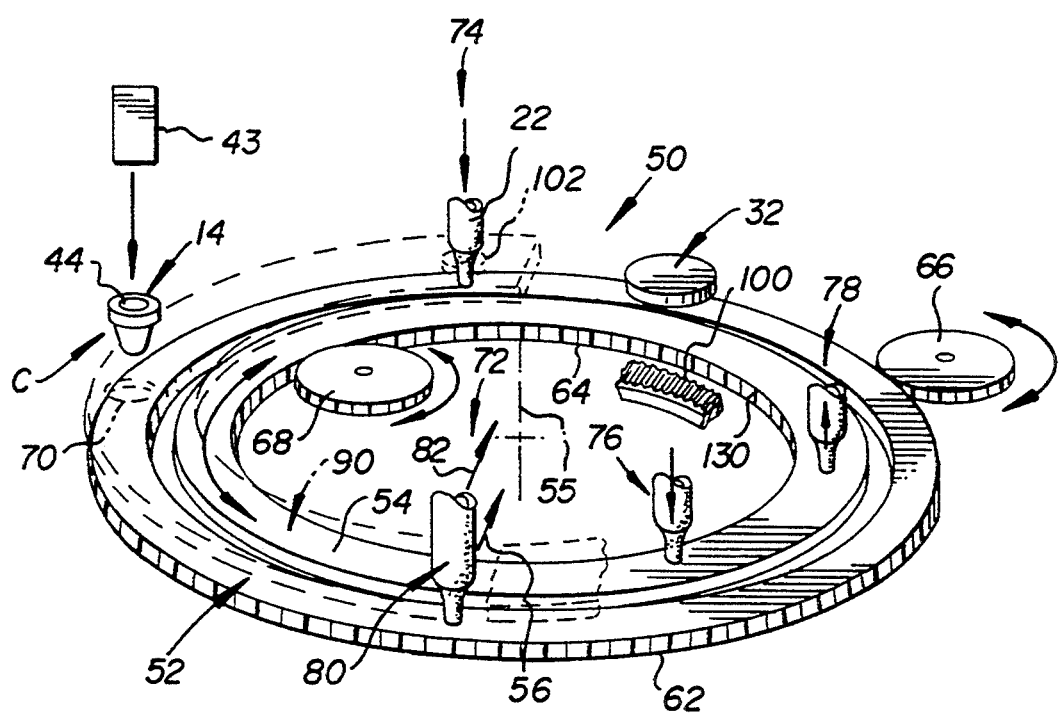
FIG. 2 is a partially schematic, isometric view of the two rotors of the incubator of the invention, showing the various stations.

As shown in FIG. 1, an analyzer 10 utilizing the incubator of the invention preferably comprises a sample supply station 12, a cuvette supply station 14, FIG. 2, a reagent supply station 16, FIG. 1, incubator 50, means 20 and 22 for transferring sample and reagent to a cuvette disposed in an outer ring of incubator 50, signal reagent supply station 24, means 26 for transferring signal reagent to the cuvette in an inner ring of incubator 50, cuvette wash station 30, and luminometer 32, all as described in commonly-owned U.S. Pat. No. 5,244,633. Any suitable construction can be used for the sample supply station 12, cuvette supply station 14, reagent supply station 16, transfer means 20, 22 and 26, signal reagent supply station 24, wash dispenser 30, and luminometer 32. Useful sample transfer devices 13 include those described and claimed in commonly owned, U.S. application Ser. No. 859,780 filed on Mar. 30, 1992 by Tomasso et al, entitled "Tray and Magnetic Conveyor", now abandoned in favor of U.S. continuation-in-part application Ser. No. 036,800, filed Mar. 25, 1993. Supply station 16 includes a rotor 34. Transfer means 20, 22 and 26 are all preferably pivoting aspirators, the aspirator at transfer means 26 having dual probes 36. Transfer means 20 preferably uses disposable tips, which can be presented for pick-up on supply station 12. Additional tips 37 can be presented on turntable 38 for use by means 20 during a dilution step. On the other hand, the aspirator for transfer means 22 preferably uses a more permanent dispensing tip, which uses a wash station 40 as is conventional.

Cuvettes can be disposed for dispensing at station 14 by mounting them in, e.g., a ring 42 that moves with rotor 16, any suitable pusher 43, FIG. 2, being used to displace a cuvette from ring 42 into incubator 50 below.

Although any cuvette can be used, preferably it is a cup-like container "C", having on its inside wall surface 44 an antibody pre-attached to the wall surface. The antibody is useful in a conventional sandwich assay which produces a complex of antibody-antigen-labeled antibody for generating a chemiluminescent signal.

The incubator is preferably that disclosed in said '633 patent, and comprises two rotors which are preferably two concentrically mounted support rings 52, 54 provided with holding apertures 57, 58, FIGS. 3 and 5, for receiving and carrying cuvettes C (delivered preferably first to ring 52 by any pusher means 43, FIG. 2), rotating means for independently rotating rings 52 and 54 about a common axis 55, transfer means 200 (FIG. 3) discussed hereinafter, for moving a cuvette, arrow 56 of FIG. 2, from ring 52 to 54, processing stations around the rings, and heating means to incubate the contents of the cuvettes on rings 52 and 54. Rings 52 and 54 are shown only schematically in FIG. 2 in association with the related components. Rotating means for the rings preferably comprise gear teeth 62, 64 disposed on each of rings 52 and 54, respectively, to be driven by pinion gears 66 and 68.

Alternatively, transfer means 200, FIG. 3, can be located elsewhere around the perimeter of the rings other than at the location shown as "56", FIG. 2.

As noted above, various processing stations are disposed around the circumference of rings 52 and 54, in addition to an entrance port 70 for cuvettes C. They are as follows, FIGS. 1 and 2: Station 72 is permanently disposed above ring 52 and is the place to which the dispensing tip 37 of aspirator 20 (not shown) pivots and descends to dispense sample into a cuvette in ring 52. First reagent addition station 74 is permanently disposed at least above ring 52 so that the permanent tip of aspirator 22 can dispense at least a first reagent into a cuvette in ring 52. Optionally, aspirator 22 can also be used to dispense a second reagent, namely a conjugate reagent, as well. A further reagent addition station 76, here for signal reagent, is disposed permanently above at least inner ring 54, to descend to dispense signal reagent into a cuvette in ring 54. Wash dispensing station 78 is disposed permanently above ring 54 for washing cuvettes using wash dispenser 30. Luminometer 32 is permanently disposed above ring 54 for reading chemiluminescence. Finally, transfer means 200 (FIGS. 3–5), discussed below, is disposed at station 80 to transfer cuvettes from ring 52 to ring 54, FIG. 2, arrow 56.

Figure 6:
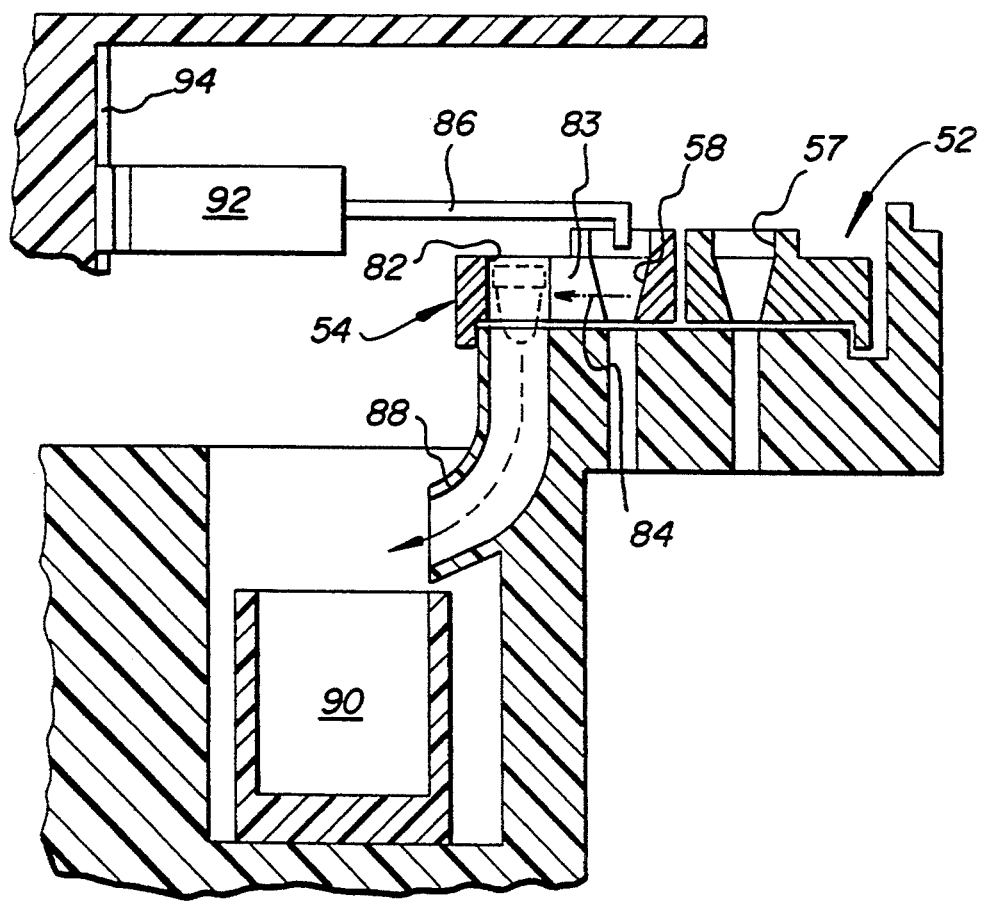
FIG. 6 is a sectional view similar to that of FIG. 3, showing an arrangement for allowing for the dumping of a used cuvette.

Final removal of the used, finished cuvette from ring 54 can be achieved by any suitable mechanism. For example, cuvettes can be pulled or cammed into an aperture 82, FIG. 6, that is interior of holding aperture 58, connected thereto by a slot 83, by sliding the cuvette radially inwardly, arrow 84, to the phantom position, using a pull rod 86 in the manner taught by U.S. Pat. No. 4,406,547. (Rod 86 is located at a peripheral position different from shuttle 200.) Aperture 82 is so much larger than each cuvette C that the latter then simply falls through chute 88 to disposal box 90. (Motor 92 for rod 86 can be indexed up and down a track 94 to move rod 86 into the cuvette.)

The details of the processing stations 30, 32, 70, 72, 74 and 76 are conventional, so that no further discussion is necessary.

Figure 5:
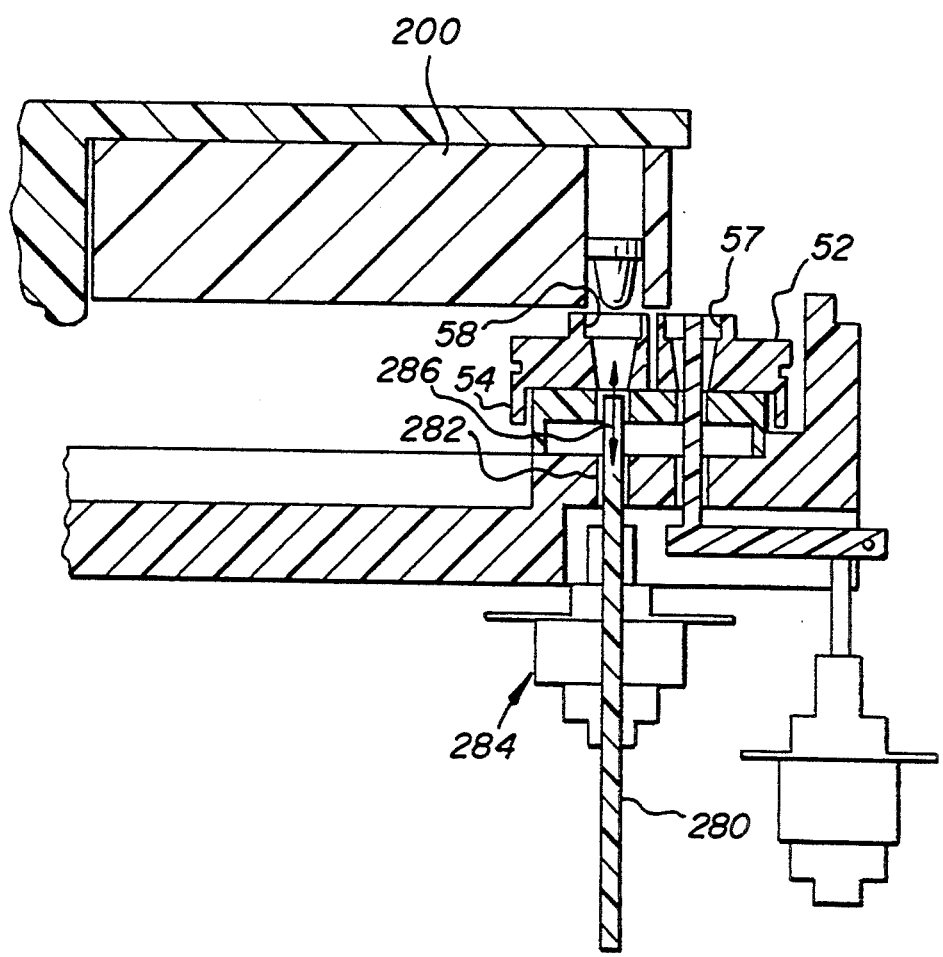
FIG. 5 is an elevational view similar to that of FIG. 3, showing the shuttle in its other position over the other rotor.

In accordance with one aspect of the invention, the transfer means 200 comprises, FIGS. 3–5, a shuttle 202 disposed above rotor rings 52 and 54. Shuttle 202 preferably has an aperture 204 or opening that is sufficiently large as to receive, without frictionally engaging, a cuvette C when such is lifted into the aperture. (As shown, aperture 204 is a through-aperture, but it can also be a hole extending upward only to level 206 shown in phantom.) That is, the interior diameter "D" of aperture 204 is just larger than exterior diameter "d" of cuvette C that, without a support underneath a cuvette, a cuvette in the aperture will fall out of it.

To allow shuttle 200 to move linearly from its position with aperture 204 aligned above ring aperture 57, to its position, FIG. 5, aligned above ring aperture 58, shuttle 200 is guided by any suitable means, such as guiding surfaces 210, 212 and guide roller 214, FIG. 4, that are part of the analyzer frame. To provide such movement relative to surfaces 210, 200 and roller 214, any suitable drive mechanism, such as a rack 220 and drive pinion 222, is useful.

To move a cuvette (preferably vertically) from its supported position in aperture 57 into aperture 204, a pusher member 230 is provided, mounted below ring 52. Specifically, an aperture 232 is provided in the frame below ring 52 to align with each of the apertures 57 as ring 52 passes thereabove. Member 230 is mounted within aperture 232, and is preferably integral with a lever arm 234 that is indexed up and down by a conventional motor, such as linear actuator motor 236. When member 230 and arm 234 are lowered, arrow 238, to the phantom position, member 230 is no longer within aperture 57 or in contact with a supported cuvette, but instead is below them.

Top surfaces 240 of rings 52 and 54 act as guide surfaces for cuvettes C as they are transferred over ring 52 to ring 54 by the movement of shuttle 200.

The method of transfer will be readily apparent from the preceding discussion. That is, a reaction cuvette C is raised out of ring 52 into shuttle 200 by first aligning aperture 204 above aperture 57, then raising member 230 to raise the cuvette into aperture 204. Shuttle 200 is then moved radially inwardly, arrow 250, FIG. 3, while the confined cuvette slides over guide surfaces 240. (Bottom edge 252 of shuttle 200 is designed to clear the top face of member 230.) As shown in FIG. 5, when aperture 204 is aligned with aperture 58, the transferred cuvette simply falls into place by gravity, into aperture 58, where it is supported and moved to stations for ring 54.

It is not necessary that anything other than aperture 58 be used to catch the following cuvette. In such a case, member 230 and guide surfaces 240 are the sole means for retaining a raised vessel within said shuttle aperture. Alternatively, however, a second pusher member 280 can be incorporated, shown in phantom, FIG. 3, and in solid lines, FIG. 5. Such a member is preferably a lead screw that operates through an aperture 282 in the analyzer frame, driven by any conventional means such as linear actuator motor 284. It is raised or lowered, arrow 286, to be in position to catch and then lower cuvette C, before it falls completely into place in aperture 58. This acts to reduce the height of fall, and thus any jarring, that might otherwise occur.

By reason of the above construction, the incubator is preferably free of any transfer means that includes a gripper that must grip, raise, lower, and then ungrip cuvette C for transfer.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. An incubator comprising a first and a second incubating rotor disposed adjacent each other, each comprising stations constructed to receive and incubate a vessel of liquid, means for independently rotating each of said rotors, and transfer means for transferring a vessel of liquid from one of said rotors to the other of said rotors;

said transfer means comprising a shuttle disposed above said rotors;

said shuttle having an aperture sufficiently large as to receive, but not retain by friction, said vessel, said shuttle being free of a gripper that grips said vessel prior to raising it from said rotor or ungrips said raised vessel after it is within said unoccupied station of said other rotor;

first means for linearly moving said shuttle so as to cause it and said aperture to traverse in a straight line from one of said rotors to the other;

a first pusher member;

second means for moving said pusher member into said one rotor into contact with a vessel in said one rotor, and for raising said contacted vessel out of its station in said one rotor into said shuttle;

said pusher member and said one rotor station being sized so as to hold a raised vessel within said shuttle aperture until said shuttle has started to move away from said one rotor;

and a guide surface under said shuttle constructed to retain said raised vessel in said aperture until a station in said other rotor is reached, so that alignment of said shuttle aperture with an unoccupied station of said other rotor is sufficient to cause said raised vessel to fall out of said aperture into said unoccupied station.

2. An incubator as defined in claim 1, wherein said rotors are disposed side-by-side in a common plane, and wherein said guide surface comprises the upper surfaces of said rotors.

3. An incubator as defined in claim 2 wherein said vessel comprises one of several reaction cuvettes containing liquid sample and reagent, and said rotor stations comprise apertures each sized to receive and hold a cuvette against falling out of said rotor.

4. An incubator as defined in claim 3, wherein said pusher member is mounted below said one rotor and wherein said second moving means include a passageway below said rotor apertures sized to allow movement of said pusher member into contact with a reaction cuvette in any one of said rotor apertures from below said rotor.

5. An incubator as defined in claim 2, wherein said pusher member is mounted below said one rotor and wherein said second moving means include a passageway below said rotor stations sized to allow movement of said pusher member into contact with a vessel in any one of said rotor stations from below said rotor.

6. An incubator as defined in claim 2 wherein said first moving means comprise a guide constraining said shuttle to move linearly across the top of said rotors, and a motor for reciprocating said shuttle linearly along said guide.

7. An incubator as defined in claim 2 wherein said guide surface and said pusher member are the sole means for retaining a raised vessel within said shuttle aperture.

8. An incubator as defined in claim 2 and further including a catcher for catching and lowering a vessel that has fallen from said shuttle aperture.

9. An incubator as defined in claim 8, wherein said catcher comprises a second pusher member mounted below Said other rotor and said other rotor includes a passageway below said stations of said other rotor sized to allow movement of said second pusher member into said apertures of said other rotor in position to catch a fallen reaction vessel.

10. An incubator as defined in claim 1 wherein said first moving means comprise a guide constraining said shuttle to move linearly across the top of said rotors, and a motor for reciprocating said shuttle linearly along said guide.

11. An incubator as defined in claim 1 wherein said guide surface and said pusher member are the sole means for retaining a raised vessel within said shuttle aperture.

12. An incubator as defined in claim 1 and further including a catcher for catching and lowering a vessel that has fallen from said shuttle aperture.

13. An incubator as defined in claim 12, wherein said catcher comprises a second pusher member mounted below said other rotor and said other rotor includes a passageway below said stations of said other rotor sized to allow movement of said second pusher member into said apertures of said other rotor in position to catch a fallen reaction vessel.

14. An incubator as defined in claim 1, wherein said vessels comprise reaction cuvettes containing liquid sample and reagent, and said rotor stations comprise apertures each sized to receive and hold a cuvette against falling out of said rotor.

15. A method for incubating a reaction vessel containing incubating liquid, said vessel being held sequentially in each of two rotors having plural stations, the method comprising the steps of a) incubating liquid in a vessel in both of said rotors, raising a reaction vessel from a station in one of said rotors to a position above said one rotor within an aperture of a shuttle, said aperture being sufficiently large as to receive, but not retain by friction, one of said vessels, c) moving said shuttle linearly while retaining the reaction vessel within said aperture from said one rotor to the other of said rotors d) and aligning said shuttle aperture with an unoccupied station of said other rotor, so that said vessel within said shuttle aperture falls into said unoccupied station.

16. A method as defined in claim 15, and further including the step of catching said falling reaction vessel with a catcher within one of said stations, and lowering said catcher and said caught reaction vessel into one of said stations.

* * * * *